United States Patent [19]
Nakao

[11] Patent Number: 5,305,755
[45] Date of Patent: Apr. 26, 1994

[54] ULTRASONIC PROBE, HAVING TRANSDUCER ARRAY CAPABLE OF TURNING AROUND ITS APERTURE AXIS AND HAVING A CONVEX LENS COMPRISING A VISCOUS RESIN

[75] Inventor: Narutaka Nakao, Kawasaki, Japan

[73] Assignee: Fujitsu Limited, Kawasaki, Japan

[21] Appl. No.: 845,716

[22] Filed: Mar. 4, 1992

[30] Foreign Application Priority Data

Mar. 12, 1991 [JP] Japan ................................. 3-46261

[51] Int. Cl.[5] .............................................. A61B 8/12
[52] U.S. Cl. ............................ 128/660.08; 128/660.10; 128/662.06; 128/663.01
[58] Field of Search .................... 128/660.01, 660.09, 128/660.08, 660.10, 660.03, 662.06, 663.01, 662.03; 310/335

[56] References Cited

U.S. PATENT DOCUMENTS

| | | | |
|---|---|---|---|
| 4,217,516 | 8/1980 | Iinuma et al. | 128/662.03 |
| 4,543,960 | 10/1985 | Harui et al. | 128/662.06 |
| 4,699,150 | 10/1987 | Kawabuchi et al. | 128/660.10 |
| 4,858,613 | 8/1989 | Fry et al. | 128/660.03 |
| 5,176,142 | 1/1993 | Mason | 128/662.06 |

Primary Examiner—William E. Kamm
Assistant Examiner—George Manuel

[57] ABSTRACT

An ultrasonic probe has a case of a substantially cylinder shape having a first axis along longitudinal direction thereof. The case has a convex wall in the vicinity of a closed end of the case. The convex wall is transparent to an ultrasonic signal radiated from the ultrasonic probe. A support cylinder having a second axis is rotatably mounted in the case. The support cylinder and the convex wall are coaxial to the second axis. An ultrasonic transducer is fixed on a base of the support cylinder. A viscous resin fills a space between the convex wall and the ultrasonic transducer. Thus, a convex lens coaxial to the second axis is formed by the convex wall and the viscous resin. The angle of the axis of the convex wall to the first axis may be chosen between zero degree to approximately 90 degrees.

8 Claims, 4 Drawing Sheets

| MATERIAL | ACOUSTIC VELOCITY c (m/s) | DENSITY $\rho$ | ACOUSTIC IMPEDANCE $\rho \times c$ (rayls) | VISCOSITY (cSt:cm Stokes) |
|---|---|---|---|---|
| PARAFFIN OIL | 1420 | 0.87 | 1.24M | 70 cSt |
| CASTOR OIL | 1500 | 0.96 | 1.44M | 7 |
| SILICONE OIL | 960~1000 | 0.8~1.0 | 0.77~1.0M | 1~1000 cSt |
| SILICONE GREASE | 1000 | 1.0 | 1.0M | 210~230 CONSITENCY |
| HUMAN BODY | approx. 1000 | | 1.5M | |
| MERITS | REFRACTIVE INDEX, LENS EFFECT | — | ACOUSTIC MATCHING | EASY HANDLING |

FIG. 6

| | LENS EFFECT | ACOUSTIC MATCHING | HANDLING |
|---|---|---|---|
| PARAFFIN OIL | NG | GOOD | NG |
| CASTOR OIL | NG | VERY GOOD | NG |
| SILICONE OIL | VERY GOOD | NOT SO BAD | NG~NOT SO BAD |
| SILICONE GREASE | VERY GOOD | NOT SO BAD | VERY GOOD |

FIG. 7

ULTRASONIC PROBE, HAVING TRANSDUCER ARRAY CAPABLE OF TURNING AROUND ITS APERTURE AXIS AND HAVING A CONVEX LENS COMPRISING A VISCOUS RESIN

BACKGROUND OF THE INVENTION

1. Field of the Invention

This invention relates to an ultrasonic diagnostic probe having a transducer array capable of turning around its aperture axis and having a convex lens comprising a viscous resin upon the aperture.

2. Description of the Related Arts

In order to diagnose an internal objects, such as an internal organ of human body, an ultrasonic tomography has been observed by the use of an ultrasonic probe which is provided with an ultrasonic transducer array for transmitting an ultrasonic sound towards the internal organ to be observed and then receiving an ultrasonic sounded reflected the internal organ. A tomographic image is obtained along the alignment of the transducer array. Some ultrasonic probes are used in contact with the surface of the human body. However, some probes are inserted as an endscope into the human body cavity where the ultrasonic transducer, i.e. the array, must be turned around its apparent axis in order to attain more objects image. Furthermore, a convex lens formed of a solid resin is provided upon the surface of the transducer array so that the ultrasonic beam is focused at a predetermined proper distance from the transducer. The ultrasonic probe used as the endscope must be of course small in size so as to be easily inserted into the body cavity. A typical prior art probe of such structure shown in FIG. 1 has been disclosed by Ito on Japanese Laid-on Patent Publication Hei 2-206450. Ultrasonic transducer 15 having a convex lens is mounted on a cylindrical support 14, 14a, and is rotatable by selectively pulling a string 22 fixed to sides of the support cylinder 14a.

Problem of the FIG. 1 probe structure is in that an O-ring 20 is required to seal between the ultrasonic transducer 12 and the probe case 16 while the ultrasonic transducer is kept rotatable along O-ring 20. The O-ring is not perfect to protect the sealing from the environment in the human body. Rotation of transducer 15 directly contacting the human organ may injure the wall of the human internal organ.

SUMMARY OF THE INVENTION

It is a general object of the invention to provide an ultrasonic probe to be inserted into a human body.

It is another object of the invention to provide an ultrasonic probe having a rotatable phased array transducer and the rotatable transducer of the probe is not directly exposed to the inner organ of the human body.

An ultrasonic probe of the present invention comprises a case in a substantially cylinder shape having a first axis along longititdinal direction thereof, the case having a convex wall in the vicinity of a closed end of the case, the convex wall being acoustically transparent for an ultrasonic signal to propagate from/to the ultrasonic probe; a support cylinder, having a second axis, rotatably mounted in the case, the support cylinder and the convex wall being coaxial to the second axis; an ultrasonic transducer fixed on a base of the support cylinder; and a viscous resin filled in a space between the convex wall and the ultrasonic transducer. A convex lens coaxial to the second axis is formed with the convex wall and the viscous resin. The axis of the convex wall may be chosen between zero degree to approximately 90 degrees to the first axis.

The above-mentioned features and advantages of the present invention, together with other objects and advantages, which will become apparent, will be more fully described hereinafter, with references being made to the accompanying drawings which form a part hereof, wherein like numerals refer to like parts throughout.

A BRIEF DESCRIPTION OF THE DRAWINGS

FIG. 1 schematically illustrates a cross-sectional view of a prior art ultrasonic probe;

FIG. 2 schematically illustrates a cross-sectional view of a first preferred embodiment of an ultrasonic probe of the present invention;

FIG. 3A and 3B schematically illustrate details of mounting a ultrasonic transducer onto a support cylinder;

FIG. 4 schematically illustrates tomographic planes at plural angular positions of the ultrasonic transducer;

FIG. 5 schematically illustrates a cross-sectional view of a second preferred embodiment.

TABLE 1 shows comparison of acoustic characteristics of candidate material for the convex lens; and TABLE 2 shows the aptitudes of available materials resulted from the TABLE 1 comparison.

DESCRIPTION OF THE PREFERRED EMBODIMENT

Figure 1:
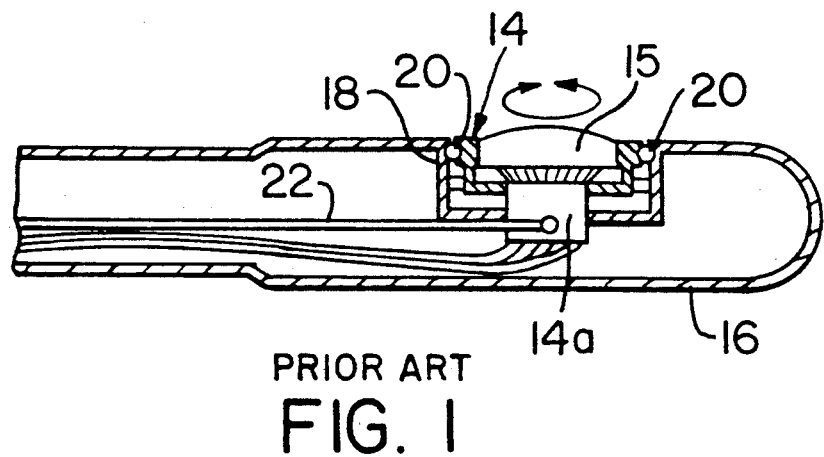

A first preferred embodiment of the present invention is hereinafter described in detail referring to FIGS. 2 through 4. An ultrasonic transducer 5 is formed of piezoelectic material, typically lead zirconate titanate $Pb(Ti,Zr)O_3$ (generally referred to as PZT) ceramic and is, for example, 10 mm in diameter and 0.5 mm thick. This ceramic disk is further saw-cut, for example 0.3 mm deep, into the substrate disk so as to form a group of 0.18 mm wide strip-shaped transducers in parallel, according to a widely known method. Electrodes, typically of metal film deposition, are formed upon each of surfaces of the strips and the opposite surface of the disk so as to apply driving voltages thereto. In a practical fabrication process the metal films are deposited on both the surfaces of the disk; next, one of the surfaces 5C having the metal film thereon is cut by a dicing saw so as to produce strip transducers having signal electrodes respectively thereon. The diameter of the outline of the metal signal electrodes is smaller than the diameter of the transducer disk so that the signal electrodes are surely insulated from the support cylinder. Another surface having metal film thereon is a ground electrode 5A common to all the strip transducers. The ground electrode 5A extends to the outer peripheral side 5B of the transducer disk. In FIG. 3(a) strip transducers are drawn on the outer surface of the transducer just for explanation, but the real transducer array has the continuous ground electrode on the outer side, and the strip electrodes are facing inside of the support cylinder 6. Outer peripheral side 5B of the transducer disk 5 is fixed into an inner step 6B provided at an inner base end of a support cylinder 6 typically of a metal material with an electrically conductive paste 13, where the extension 5B of the ground electrode allows a sure contact with the support cylinder 6. The ground electrode faces outwards. Each of the signal electrodes faces inward so as to be connected to a wiring, typically formed on a flexible printed circuit 12, inside the support cylinder 6.

Case 1 is formed of a resin material, such as PPO (polyphenylene oxide), which is transparent for an ultrasonic wave to propagate therethrough, and consists of an upper half 1A and a lower half 1B, cut along the axis of the cylinder shape of case 1. Near the top end of upper half 1A, the wall of the case is made as thin as 0.5 mm and spherically embossed outwards so as to form a convex wall denoted with 1C. When the upper and lower halves 1A and 1B are assembled, i.e. glued, the top end 1D of case 1 is closed and is shaped round so that the case can be smoothly inserted into a cavity of human body.

Before the upper and lower halves are glued and before support cylinder 6 is installed in cylindrical hole 1E, a viscous resin, for example, a silicone grease 3, is poured into the inside of the convex wall 1C. Next, the base end, having the transducer, of the support cylinder 6 is inserted into a cylindrical hole 1E cut in upper half 1A of the case. Thus, the silicone grease fills up the space between the convex wall 1C and transducer disk 5 so that the silicone grease together with convex wall 1C forms a convex lens. Cylindrical hole 1E and the convex wall 1C are coaxial with each other. Thus, convex lens and the transducer disk is coaxial with each other. The silicone grease which is a little excessive over the volume to fill the space penetrates into the gap 11 between the support cylinder 6 and cylindrical hole 1E, where the support cylinder 6 is smoothly rotatable around the axis of the cylinder. The quantity of the silicone grease has been chosen so that the grease does not excessively flow out of the gap 11 owing to its properly high viscosity. Another end of the support cylinder 6 is supported by a ball bearing 9 provided on the lower half 1B in order to ensure a smooth and reliable rotation of the support cylinder. A part of the peripheral surface of the support cylinder is provided with a pulley 7, on which a string 8 is engaged so that the support cylinder is controlled to rotate from the other open end of the cylindrical case 1 by pulling a proper end of string 8.

Signal lines 12 typically formed of a flexible printed circuit board are electrically connected to each of the signal electrodes. A ground line 11A is connected to a portion of inside wall 6A of the support cylinder 6. The inner side of the transducer disk 5 is provided with a backing material, typically formed of a resin (not shown in the figures), which also mechanically fixes signal lines 12 and ground line 11A. Signal lines 12 and ground line 11A are arranged adequately flexible to be durable for the frequent rotation of the support cylinder.

Comparison of acoustic characteristics of candidate viscous material and the object human body are shown in Table 1. To attain a good lens characteristics, the acoustic velocity of the lens material has to be far different from that of the human body. can be employed to form the convex lens. To attain a good acoustic matching of the transducer with the human body, the acoustic impedance of the material has to be close to that of the human body. To achieve an easy assembling operation of the probe, the more viscous material is preferable. That is, the liquid materials, such as paraffin oil, caster oil and silicone oil, are difficult to handle in the assembling operation. Considering all of the required characteristics, the aptitudes of the available viscous materials to form the convex lens are shown in Table 2. As a result, it is determined that the silicone grease is the most preferable. Among many of available silicone grease, Toray silicone SH111 was employed by the inventor for this purpose.

Figure 2:
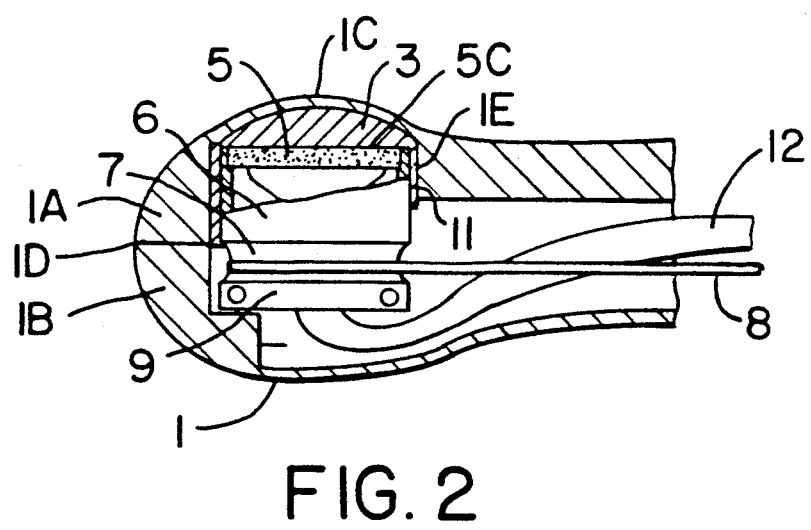
Figure 3A:
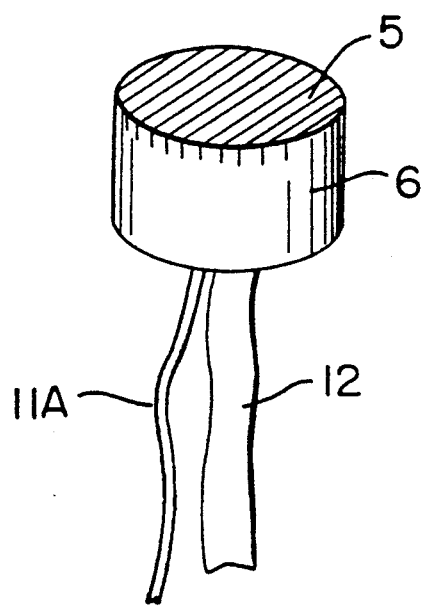
Figure 3B:
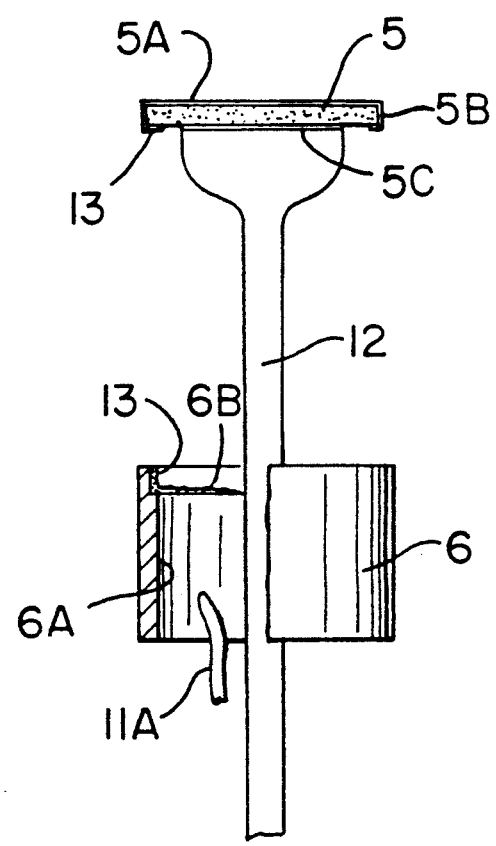

Though in FIGS. 2 the axis of the transducer aperture, i.e. axis of the transducer rotation is drawn approximately orthogonal to the longitudinal axis of the case, the direction of the aperture of the transducer can be arbitrarily chosen. In other words, the angle of the aperture axis to the axis of case 1 may be chosen from zero to any angle equal to or more than 90 degrees upon the design requirement.

Due to the shorter length of strip-shaped transducer at the peripheral ends of the aligned strips, the ultrasonic beam radiation from each strip electrode is well weighted so as to eliminate undesirable side-lobes. Together with the focussing function of the convex lens this preferable characteristic of the strip transducers provides a good resolution of the probe at a distance of the objects from the transducer.

Figure 4:
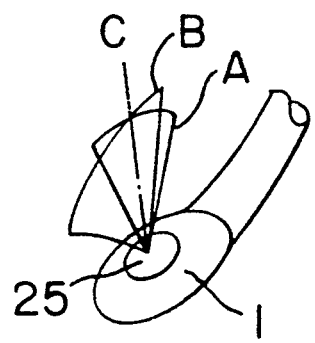

The tomographic planes A and B, which the transducer can observe at different two angles, 90° from each other, are representatively shown in FIG. 4, where the axis of the transducer aperture is denoted with C. Any other angular position of the tomographic plane can be chosen by rotating the ultrasonic transducer, so that the object in the human body can be precisely observed.

Thus, according to the present invention, there is accomplished an ultrasonic probe adequately small as well as reliably sealed from the human organ to which the probe is inserted. The human organ is fully protected from the direct contact of the rotating transducer. Moreover, the assembling process of the probe can be quite simple.

Figure 5:
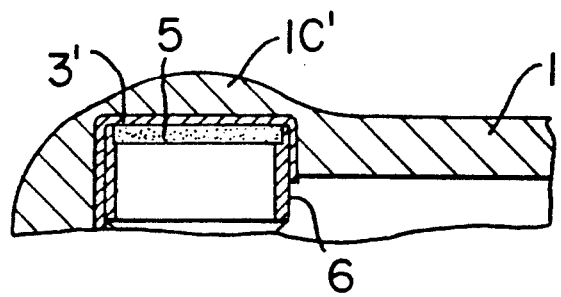

Referring to FIG. 5, a second preferred embodiment of the present invention is hereinafter described. The distinction of the second preferred embodiment is in that the convex wall 1C which is uniformly thin in the first preferred embodiment is modified so as to have a convex cross-section 1C', that is, thicker at the center. Thus, the convex wall 1C' and silicone grease 3' filled between the convex wall 1C' form a convex lens for transducer 5. Silicone grease 3' also performs as a lubricant between the convex wall and transducer 5. The probe of the second preferred embodiment can enjoy the same advantageous effects of the first preferred embodiment.

The many features and advantages of the invention are apparent from the detailed specification and thus, it is intended by the appended claims to cover all such features and advantages of the methods which fall within the true spirit and scope of the invention. Further, since numerous modifications and changes will readily occur to those skilled in the art, it is not detailed to limit the invention and accordingly, all suitable modifications are equivalents may be resorted to, falling within the scope of the invention.

What I claim is:

1. An ultrasonic probe comprising:
   a case of a substantially cylinder shape having a first axis along longitudinal direction thereof, said case having a thin convex wall in the vicinity of a closed end of said case, said convex wall being acoustically transparent for an ultrasonic signal to radiate from the ultrasonic probe;
   a support cylinder having a second axis rotatably mounted in said case, said support cylinder and said convex wall being coaxial to said second axis;

an ultrasonic transducer of phased-array type and including a plurality of transducer elements, said ultrasonic transducer being fixed on a base of said support cylinder; and a viscous resin filled in a space between said convex wall and said ultrasonic transducer so that a convex lens coaxial to said second axis is formed by said convex wall and said viscous resin, said viscous resin also filling a gap between a case wall and said support cylinder for rotatably supporting said support cylinder in said case.

2. An ultrasonic probe as recited in claim 1, wherein said convex wall is of a uniform thickness embossing outwards.

3. An ultrasonic probe as recited in claim 1, wherein said convex wall is in a shape of a convex lens.

4. An ultrasonic probe as recited in claim 1, wherein said convex wall is located at a side of said case, said second axis being approximately orthogonal to said first axis.

5. An ultrasonic probe as recited in claim 1, wherein said transducer elements are strip transducers aligned in parallel with each other and orthogonal to said second axis, each of said strip transducers being electrically driven to form a phased-array so that objects in a plane including said second axis and a strip transducers alignment are tomographically observed.

6. An ultrasonic probe as recited in claim 3, wherein the outline of said plural strip ultrasonic transducers is circle, and fits said base of said support cylinder.

7. An ultrasonic probe as recited in claim 1, wherein the focal length of said convex lens is chosen at a distance of object an to be observed.

8. An ultrasonic probe as recited in claim 1, wherein said viscous resin is a silicone resin.

* * * * *